United States Patent
Trotzschel et al.

(10) Patent No.: US 8,349,248 B2
(45) Date of Patent: Jan. 8, 2013

(54) METALLIC MATERIAL AND METHODS OF MAKING AND USING SAME

(75) Inventors: Jens Trotzschel, Bruchkobel (DE); Bernd Spaniol, Hammersbach (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 489 days.

(21) Appl. No.: 11/279,669

(22) Filed: Apr. 13, 2006

(65) Prior Publication Data

US 2006/0169364 A1    Aug. 3, 2006

Related U.S. Application Data

(63) Continuation of application No. PCT/EP2004/010904, filed on Sep. 30, 2004.

(30) Foreign Application Priority Data

Oct. 17, 2003  (DE) .................................. 103 49 102
Jul. 1, 2004   (DE) .......................... 10 2004 032 128

(51) Int. Cl.
    *C22C 27/02* (2006.01)
(52) U.S. Cl. ........ 420/425; 420/417; 420/418; 420/419; 420/420; 420/421; 420/422; 420/423; 420/424; 420/426; 420/427; 420/428; 420/430; 148/668; 148/669; 148/671; 148/672; 148/673; 148/674; 148/675; 148/677
(58) Field of Classification Search .......... 148/668–675, 148/677; 420/421–430
See application file for complete search history.

(56) References Cited

U.S. PATENT DOCUMENTS

| | | | |
|---|---|---|---|
| 2,987,352 A | 6/1961 | Watson | |
| 4,526,629 A | 7/1985 | Latta et al. | |
| 5,098,485 A | 3/1992 | Evans | |
| 5,242,481 A | 9/1993 | Kumar | |
| 6,165,623 A * | 12/2000 | Fife et al. | 428/472 |
| 6,358,625 B1 * | 3/2002 | Kumar et al. | 428/553 |
| 6,521,173 B2 | 2/2003 | Kumar et al. | |
| 6,545,858 B1 | 4/2003 | Naito et al. | |
| 2004/0149356 A1 | 8/2004 | Spaniol | |
| 2007/0017611 A1 | 1/2007 | Spaniol | |

FOREIGN PATENT DOCUMENTS

| | | |
|---|---|---|
| JP | 63090315 A | 4/1988 |
| JP | 7183167 A | 7/1995 |
| JP | 11264064 A | 9/1999 |
| WO | 02/098275 A2 | 12/2002 |
| WO | 03/008657 A1 | 1/2003 |

OTHER PUBLICATIONS

Joshi et al., "Surface Segregation of Oxygen in Nb-o and ta-o Alloys", *Scripta Metallurgica*, vol. 8, pp. 413-424, (1974).
Cost, "On the Existence of Interstitial Clustering of Oxygen in Nb-O Solid Solutions", *Acta Metall.*, vol. 32, No. 1, pp. 123-130 (1984).
Office Action Issued Aug. 24, 2006 in U.S. Appl. No. 10/759,692.
Office Action Issued Jan. 11, 2007 in U.S. Appl. No. 10/759,692.
"Werkstoffkunde der Hochvakuumtechnik," Band 1, VEB Deutscher Verlag der Wissenschaften, Dr. Wener Espe, Berlin, 1959.
Arfaoui et al. "Evidence for a large enrichment of interstitial oxygen atoms in the nanometer-thick metal layer at the NbO/Nb (110) interface", Journal of Applied Physics, vol. 91, No. 11, Jun. 1, 2002.
Office Action Issued Sep. 30, 2008 in U.S. Appl. No. 11/528,110.
Office Action Issued Jun. 25, 2009 in U.S. Appl. No. 11/528,110.
Office Action Issued Dec. 8, 2010 in U.S. Appl. No. 11/528,110.
Office Action Issued Jun. 22, 2010 in U.S. Appl. No. 11/528,110.
U.S. Office Action issued Jun. 24, 2011 in U.S. Appl. No. 11/528,110.
Perkins et al: "Oxygen Diffusion in Niobium and Nb-Zr Alloys"; Acta Metallurgica; 25 (10); pp. 1221-1230; Pergamon Press (1977).

* cited by examiner

*Primary Examiner* — Lois Zheng
(74) *Attorney, Agent, or Firm* — Panitch Schwarze Belisario & Nadel LLP

(57) ABSTRACT

A metallic material is made from at least one refractory metal or an alloy based on at least one refractory metal. The metallic material has an oxygen content of about 1,000 to about 30,000 µg/g and the oxygen is interstitial.

8 Claims, No Drawings

METALLIC MATERIAL AND METHODS OF MAKING AND USING SAME

CROSS-REFERENCE TO RELATED APPLICATIONS

This application is a continuation of International Application No. PCT/EP2004/010904, filed Sep. 30, 2004, which was published in the German language on Apr. 28, 2005, under International Publication No. WO 2005/037468 A2, and the disclosure of which is incorporated herein by reference.

BACKGROUND OF THE INVENTION

The invention relates to a metallic material comprising at least one refractory material or an alloy based on at least one refractory material. The invention also relates to the manufacture and use of the metallic material.

Particularly in the area of medical technology, wires, pipes, or bands made of noble metals (e.g., platinum or platinum alloys) or of refractory metals Y of the group (chromium, cobalt, molybdenum, nickel, niobium, rhenium, tantalum, titanium, wolfram, zirconium) and their alloys (for example, NbZr1 (1 wt % Zr) or $TaNb_xY_z$ (where x and z represent possible atomic ratios of Nb and Y)), as well as stainless steels or nitinol, are used for a variety of purposes. Most metallic materials which find use for various medical applications represent a compromise between good compatibility, handlability, good mechanical properties, workability, and the associated costs.

The requirements for materials, such as used for stents, are many. Materials are needed with the highest rigidity possible. High rigidity allows the required strut cross-sections to be reduced to an appropriate minimum. The criterion here is to achieve the highest possible supporting effect with the lowest possible amount of material introduced into the human body. Reduction of the amount of metal also results in improvement of the core spin compatibility of the stent, since less material results in fewer artifacts during examination with core spin tomography.

At the same time, with the reduction in the amount of material, however, the visibility of the parts (for example, stents) is decreased in an X-ray image. This disadvantage can be avoided by providing a layer of highly X-ray-visible material (generally a noble metal with a high atomic number) on the structure, or equipping it with so-called markers. In both cases, there is a certain risk that this application may create corrosive potentials between the different materials, which can lead to the weakening or dissolution of the parts affected.

Some known materials for stents (stainless steel, CoCr alloys, MP35N or nitinol) are generally not helpful, or contain additional chemical components that are not considered biocompatible.

Refractory metals exhibit relatively good X-ray contrast. In addition, there are many combinations in which they are soluble in each other, allowing the possibility of varying the X-ray contrast and adjusting it specifically.

Metallic materials of the type characterized above are known, for example, from U.S. Pat. No. 6,358,625 B1. Here, anode wires of niobium or tantalum are disclosed, which are treated with oxygen to improve the bond, in such a way that an enrichment results on the surface in the range of 35 atomic % in a layer of about 50 nm thick. This enrichment produces a surface layer with niobium oxide or tantalum oxide, which is used as a sintering aid in the manufacture of capacitors.

Espe, *Materials Science of High-Vacuum Technology*, vol. 1, pages 146 through 149, VEB German publisher of the German sciences, Berlin (1959) describes a surface oxidation of niobium, wherein a brittleness of the material is introduced with increasing oxygen uptake, whereby the ductility of the material therefore decreases. In particular, the reduction in elongation at break can be seen in Table T3.7-2b. Thus, this teaching also recommends the reduction of oxygen.

From U.S. Pat. No. 5,242,481, in agreement with the disclosure of Espe, powder-metallurgically manufactured products of tantalum or niobium are known, which have an oxygen content of less than 300 µg/g. Likewise in agreement therewith, it is known from German published patent application DE 37 00 659 A1 that tantalum becomes brittle if it is exposed to oxygen-containing atmospheres at higher temperatures. It thereby loses its ductility.

BRIEF SUMMARY OF THE INVENTION

An object of the present invention is to improve the properties of the known materials made of refractory metal or an alloy based on a refractory metal, particularly their mechanical properties, such as ductility. It is also an object of the invention to provide a process for the manufacture of these metals and suitable uses.

The object of the invention is achieved in that the metallic material has an oxygen content of approximately 1,000 to about 30,000 µg/g and that the oxygen is interstitial. Surprisingly good mechanical properties result therefrom, including high tensile strength and ductility, at room temperature or in the vicinity of room temperature, despite (or precisely due to) the high oxygen content, which according to traditional theory and general experience would instead lead to brittleness in the material and thus to a reduction in ductility. This previous assumption, among other things, is the reason that the standards ASTM B362 (for niobium and NbZr1) and ASTM F560 (for tantalum), used for applications of refractory metals in medical technology, limit the maximum permissible oxygen content to values between 100 and 400 ppm. The corresponding manufacturing processes for this type of metal are consequently designed in such a way that oxygen uptake for the material is substantially excluded during processing.

DETAILED DESCRIPTION OF THE INVENTION

The now discovered theory specifically uses oxygen for the improvement of properties, thus opening the possibility of significantly broadening the range of applications of refractory metals and their alloys in medical technology and in other areas. To explain the targeted effect, it is assumed that the interstitial oxygen drastically reduces the mobility of dislocation. Consequently, there is probably formation of a higher density of dislocation, during the plastic deformation. The number of these dislocations, the degree of deformation, and the oxygen content or the content of other interstitial impurities or doping influence the mechanical properties. After later re-crystallization, additional grains are thereby formed, thus generating a fine-grained structure advantageous for the mechanical properties.

For this purpose, it is advantageous that the oxygen be distributed homogeneously. An oxygen content of approximately 1,000 µg/g to 15,000 µg/g is beneficial, preferably around 8,000 µg/g. It is further expedient for the refractory metal to be selected from the group of titanium, niobium, zirconium, molybdenum, tantalum, tungsten, and rhenium. It can be alloyed with an additional refractory metal, particularly another metal from this group. The metallic material can be doped with one or more chemical elements of the group P, S, V, Y, La, Hf, Ce, and Th. It is beneficial for the material to have a tensile strength of at least 700 mPa at an elongation of about 20 to 30%.

The material according to the invention can be manufactured using a process in which it is enriched with oxygen at about 600 to 800° C. and an oxygen partial pressure of <5 mbar. In particular, the process can take place in an oxygen-containing gas. The material can also be manufactured by forming an oxide layer, preferably amorphous, on or at its surface, and thereafter a diffusion annealing is performed, by which the oxygen penetrates into the depth of the material. Since amorphous oxide layers diffuse more easily into the material, the diffusion should occur at least as quickly as oxide formation on the surface. Here, it is advantageous for the oxide layer to be formed by wet chemistry, particularly by anodic oxidation, or thermally, particularly by surface oxidation under an oxygen atmosphere.

Alternatively, the material can also be manufactured by forming the refractory metal or the alloy with a sintering process, wherein oxygen is introduced. This is possible, for example, by sintering of oxide powder.

Preferably, the metallic material is subjected to deformation after the oxygen enrichment, wherein the deformation preferably occurs up to the critical degree of deformation. The critical degree of deformation for any material is the specific degree of deformation that is the minimum necessary for a resecondary crystallization during a subsequent heat treatment. Here, it is advantageous for the deformation to occur in multiple steps.

According to the invention, the metallic material can be used for the manufacture of medical products, particularly for the manufacture of implants. The material can also be used for the manufacture of semi-finished products, particularly wires, pipes, or bands, which are used for the manufacture of orthopedic implants, heart pacemaker components, stimulation electrodes, guide wires, or stents.

The invention will now be explained further below with reference to the following specific, non-limiting examples.

Niobium or NbZr1 or tantalum with interstitially dissolved oxygen can be used very well as material for medical products to be implanted. For niobium or NbZr1 in the fully recrystallized material state, ultimate tensile strengths between 750 MPa and 1,200 MPa are achieved at elongations in a range of 20% to 30%, if these materials exhibit an oxygen content of at least 1,000 μg/g. In comparison thereto, non-oxygen-loaded niobium or NbZr1 in the recrystallized state achieves only strengths of between 275 MPa and 350 MPa at comparable elongation values. If these materials are deformed, they exhibit a high strength at only low elongation values (for example, about 700 Mpa at an elongation<1%).

EXAMPLE 1

Manufacture of a Niobium Wire

A precursor material (wire) is produced with a diameter of up to about 2.15 mm. Thereafter, oxygen loading is performed using annealing at an oxygen partial pressure of about $2\times10^{-3}$ mbar at a temperature of 700° C. over a period of 10 hours. This is followed by a homogenization annealing in a high vacuum (<$10^{-4}$ mbar) at a temperature of about 900° C. over a period of about one hour. The wire is then deformed (drawn or rolled), with at least the critical degree of deformation, to a diameter of 0.24 mm. Finally, a recrystallization annealing is performed. The resulting wire has an oxygen content of 5,000 μg/g. It exhibits a tensile strength of 900 MPa at an elongation $A_{L254}$ of 25%. Elongation $A_{L254}$ is the measured elongation relative to a starting length $L_0$ of 254 mm.

EXAMPLE 2

Manufacture of a NbZr1 Wire (1% by Weight Zr)

The manufacture of the precursor wire is performed with a diameter of 2.15 mm. Thereafter, oxygen loading is performed using electrochemical oxidation. An oxide film thickness of approximately 400 to 500 nm is achieved. Next, a homogenization annealing is performed in a high vacuum (<$10^{-4}$ mbar) at a temperature of about 900° C. over a period of about one hour. The wire is then deformed (drawn or rolled), with at least the critical degree of deformation, to a diameter of 0.24 mm. Finally, a recrystallization annealing is performed. The wire manufactured in this manner has an oxygen content of about 500 to 3,000 μg/g. It has a tensile strength of 900 to 1,100 MPa at an elongation $A_{L254}$ of 20 to 25%.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A wire consisting essentially of a metallic material comprising at least one refractory metal or an alloy based on the at least one refractory metal,
wherein the metal or alloy has an oxygen content of approximately 5,000 to 30,000 μg/g and wherein the oxygen is interstitial and is distributed homogeneously.

2. The wire according to claim 1, wherein the at least one refractory metal is selected from the group consisting of titanium, niobium, zirconium, molybdenum, tantalum, tungsten, and rhenium.

3. The wire according to claim 1, wherein the metal or alloy is doped with at least one element selected from the group consisting of P, S, V, Y, La, Hf, Ce, and Th.

4. The wire according to claim 1, wherein the material exhibits an ultimate tensile strength of between 750 and 1,200 MPa at an elongation of about 20 to 30%.

5. A pipe consisting essentially of a metallic material comprising at least one refractory metal or an alloy based on the at least one refractory metal, wherein the metal or alloy has an oxygen content of approximately 5,000 to 30,000 μg/g and wherein the oxygen is interstitial and is distributed homogeneously.

6. The pipe according to claim 5, wherein the at least one refractory metal is selected from the group consisting of titanium, niobium, zirconium, molybdenum, tantalum, tungsten, and rhenium.

7. A band consisting essentially of a metallic material comprising at least one refractory metal or an alloy based on the at least one refractory metal, wherein the metal or alloy has an oxygen content of approximately 5,000 to 30,000 μg/g and wherein the oxygen is interstitial and is distributed homogeneously.

8. The band according to claim 7, wherein the at least one refractory metal is selected from the group consisting of titanium, niobium, zirconium, molybdenum, tantalum, tungsten, and rhenium.

* * * * *